June 20, 1972 L. P. PRATT Plant Pat. 3,217

PEACH TREE

Filed Nov. 16, 1970 2 Sheets-Sheet 1

INVENTOR
LESTER P. PRATT
BY Christensen, Sanborn & Matthews
ATTORNEYS

INVENTOR
LESTER P. PRATT
BY Christensen, Sanborn & Matthews
ATTORNEYS

United States Patent Office

Plant Pat. 3,217
Patented June 20, 1972

3,217
PEACH TREE

Lester P. Pratt, Wenatchee, Wash., assignor to Van Well Nursery, Inc., Wenatchee, Wash.

Filed Nov. 16, 1970, Ser. No. 90,163
Int. Cl. A01h 5/03
U.S. Cl. Plt.—43 1 Claim

ABSTRACT OF THE DISCLOSURE

As a mutation of Redhaven, a new peach tree variety is disclosed which is characterized by its semidwarf nature and the vigorous growth of the lateral buds near the base of its terminal shoots.

*Description*

This invention or discovery relates to a new and distinct variety of peach tree originating as a sport or mutation of the variety which has long been sold in commerce under the name Redhaven (unpatented), the discovery having been made in applicant's cultivated orchard near Orondo, Douglas County, Wash.

The new variety is of semidwarf growth characteristics which makes it possible to plant at closer spacings than can be done with its parent variety, Redhaven. The tree differs from its parent not only in size but in the outstanding vigorous growth and fruit bearing capabilities of lateral buds along substantially all terminal shoots. The vigorous growth of these lateral buds is such, particularly near the bases of terminal shoots, that the base diameters of most such lateral buds range from one-half to three-fourths that of the base of the terminal shoots from which they branch. Also, the growth extensions of these lateral buds most often range from one-half to three-fourths the growth extension of the supporting terminal shoot itself and occasionally equal the length of the terminal shoot. In contract, growth of the lateral buds near the base of the terminal shoot growth of the standard Redhaven are most often sparse, small and spindly and incapable of bearing fruit. The outstanding growth characteristics of applicant's new variety permits the maintenance of excellent fruiting wood on the lower branches of the tree.

Applicant has asexually reproduced his new variety in his orchard near Orondo, Douglas County, Wash., by means of budding and its outstanding characteristics appear to be permanent.

Figure 1:
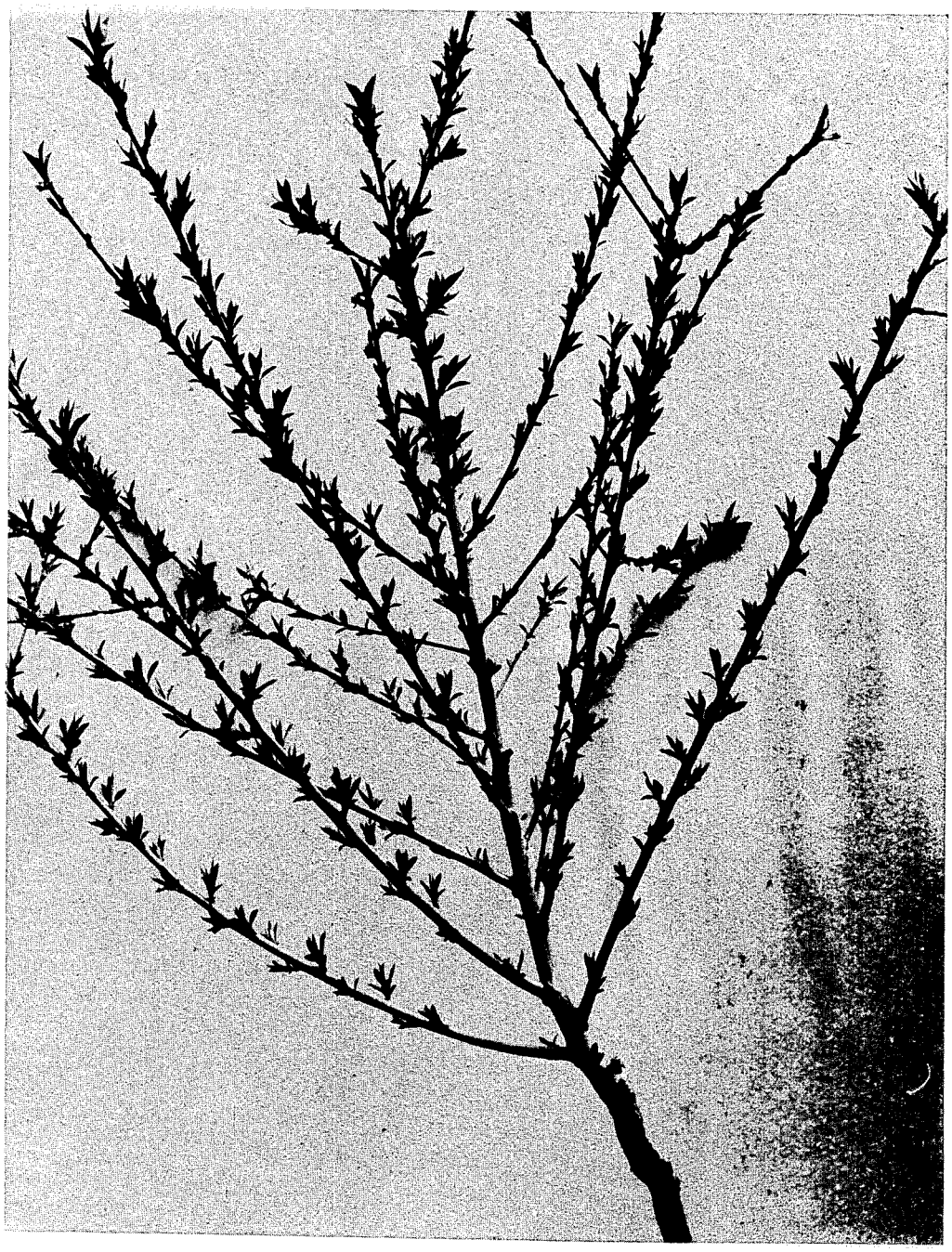
Figure 2:
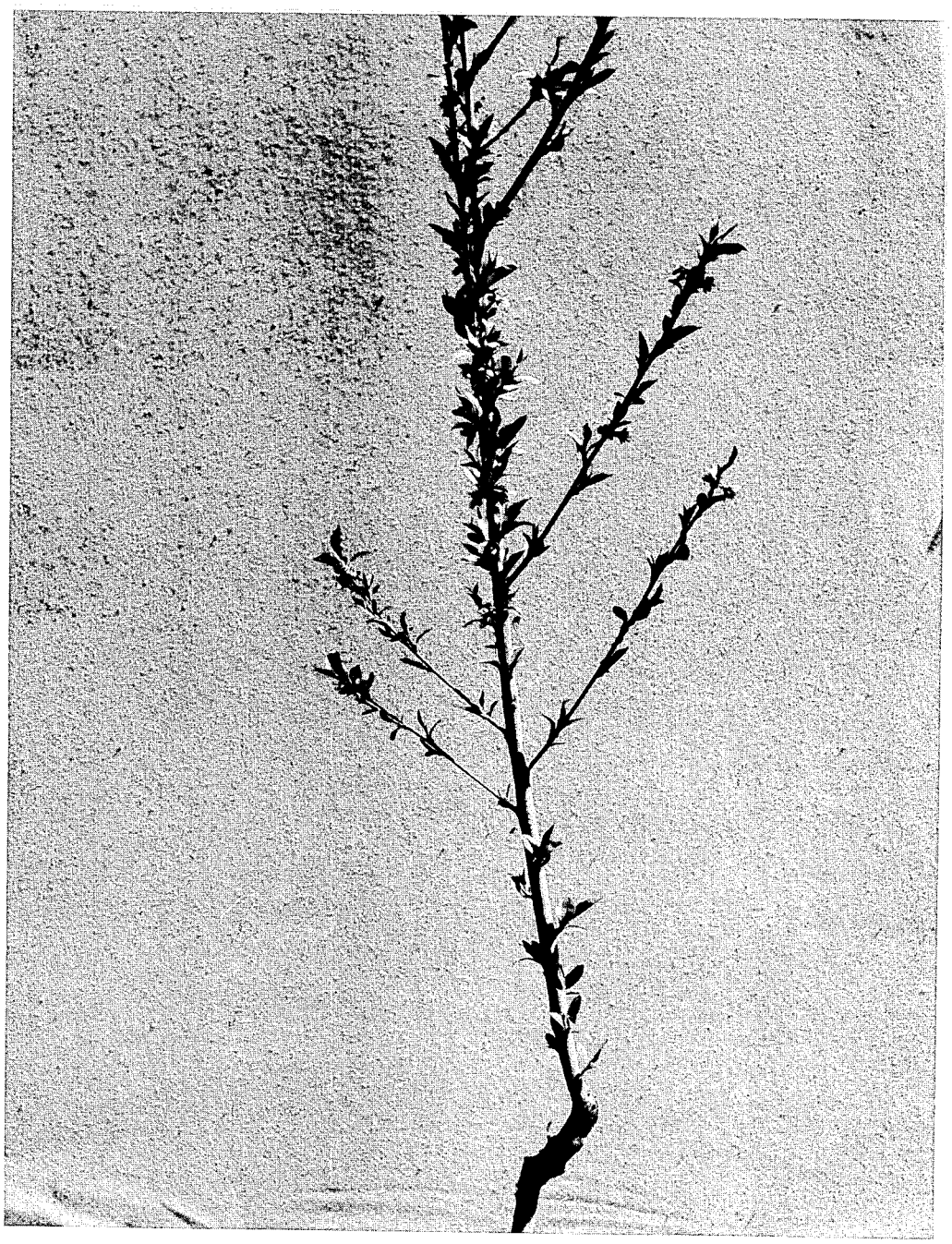

FIG. 1 is a photograph of a typical branch of the new variety illustrating the vigorous growth of the lateral buds, particularly near the base of the terminal shoot and their relative growth, FIG. 2 is a photograph of a typical Redhaven branch for comparison.

Tree: Medium small; semidwarf; moderately vigorous compact form. Height 7 feet; spread 7 feet. Adjacent Redhaven tree of same age, height 12 feet; spread 8 feet.

Flowers and leaves: Identical to the standard Redhaven.

Fruit: Similar in shape and size and matures at the same time as Redhaven. Colored similarly to Redhaven, namely, red color all over with red color fully developing in shaded areas of tree.

I claim:

1. A new and distinct variety of peach tree characterized as to novelty primarily by the semidwarf nature of its growth characteristics, particularly by the vigorous growth of the lateral buds near the base of the terminal shoot growth, clearly distinguishable from its parent, which is the nearest related variety, the Redhaven, substantially as shown and described.

No references cited.

ROBERT E. BAGWILL, Primary Examiner